United States Patent
Fujiwara et al.

(10) Patent No.: US 8,765,115 B2
(45) Date of Patent: Jul. 1, 2014

(54) METHOD OF TREATMENT OF GASTROINTESTINAL DISORDERS WITH IL-10

(75) Inventors: Yoshihiro Fujiwara, Tsukuba (JP); Kenji Sekikawa, Tsukuba (JP); Fumio Takaiwa, Tsukuba (JP); Noriko Tsuji, Tsukuba (JP)

(73) Assignees: National Institute of Agrobiological Scienses, Ibaraki (JP); Preventec, Inc., Ibaraki (JP); National Institute of Advance Industrial Science & Technology, Tokyo (JP)

( * ) Notice: Subject to any disclaimer, the term of this patent is extended or adjusted under 35 U.S.C. 154(b) by 0 days.

(21) Appl. No.: 13/307,782

(22) Filed: Nov. 30, 2011

(65) Prior Publication Data

US 2012/0328561 A1    Dec. 27, 2012

Related U.S. Application Data

(60) Provisional application No. 61/418,481, filed on Dec. 1, 2010.

(51) Int. Cl.
*A61K 38/20* (2006.01)
*C07K 14/54* (2006.01)
*C12N 15/82* (2006.01)

(52) U.S. Cl.
CPC ......... *A61K 38/2066* (2013.01); *C07K 14/5428* (2013.01); *C12N 15/8242* (2013.01); *C12N 15/8257* (2013.01)
USPC ........................................ 424/85.2; 424/750

(58) Field of Classification Search
CPC ........... A61K 38/2066; C07K 14/5428; C12N 15/8242; C12N 15/8257
USPC ................................................. 424/85.2, 750
See application file for complete search history.

(56) References Cited

U.S. PATENT DOCUMENTS

2012/0142033 A1    6/2012    Fujiwara et al.

FOREIGN PATENT DOCUMENTS

JP    2010-183904    8/2010

OTHER PUBLICATIONS

Nakase H et al., J Gastroenterology, Mar. 2003;38 Suppl 15:59-62.*
Ming-Cai Li et al, World J Gastroenterol Mar. 1, 2004;10(5):620-625.*
Frossard et al (2007) J. Allergy Clin Immunol, 119:952-959.*
Kevin W. Moore, et al., "Interleukin-10 and the Interleukin-10 Receptor", Annual Review of Immunology, 2001, vol. 19, pp. 683-765.
K. Asadullah, et al., "Interleukin-10 Therapy-Review of a New Approach", Pharmacological Reviews, 2003, vol. 55, pp. 241-269.
Stefan Schillberg, et al., "'Molecular farming' of antibodies in plants", Naturwissenschaften, Feb. 18, 2003, vol. 90, pp. 145-155.
Fumio Takaiwa, et al., "Endosperm tissue is good production platform for artificial recombinant proteins in transgenic rice", Plant Biotechnology Journal, 2007 vol. 5, pp. 84-92.
Andre Franke, et al., "Sequence variants in IL10, ARPC2 and multiple other loci contribute to ulcerative colitis susceptability", Nature Genetics, Nov. 2008, vol. 40, pp. 1319-1323.
Edouard Louis, et al., "Genetics of ulcerative colitis: the come-back of interleukin 10", Gut, Sep. 2009, vol. 58, No. 9, pp. 1173-1176.
Noriko M. Tsuji, et al., "Oral tolerance: intestinal homeostasis and antigen-specific regulatory T cells", Trends in Immunology, Oct. 4, 2008, vol. 29, No. 11, pp. 532-540.
Erik-Oliver Glocker, et al., "Inflammatory Bowel Disease and Mutations Affecting the Interleukin-10 Receptor", New England Journal of Medicine, Nov. 19, 2009, 361:21, pp. 2033-2045.
Yoshihiro Fujiwara, et al., "Extraction and purification of human interleukin-10 from transgenic rice seeds", Protein Expression and Purification, 2010, vol. 72, pp. 125-130.

* cited by examiner

*Primary Examiner* — Prema Mertz
(74) *Attorney, Agent, or Firm* — Cook Alex Ltd.

(57) ABSTRACT

Providing a new method of treating inflammatory gastrointestinal disorders and a food product for the prevention or improvement of inflammatory gastrointestinal disorders. Prevention or treatment of inflammatory gastrointestinal disorders is possible by oral administration of recombinant IL-10 expressed in rice plant seeds.

8 Claims, 7 Drawing Sheets

FIG. 1

```
         10         20         30         40         50         60
AGTCCAGGCCAAGGAACTCAGTCTGAAAATAGCTGCACACACTTCCCTGGCAATCTCCCA
 S  P  G  Q  G  T  Q  S  E  N  S  C  T  H  F  P  G  N  L  P 70         80         90        100        110        120
AACATGCTTCGTGATTTGAGGGATGCATTCAGTCGTGTTAAGACCTTCTTTCAAATGAAG
 N  M  L  R  D  L  R  D  A  F  S  R  V  K  T  F  F  Q  M  K 130        140        150        160        170        180
GATCAACTAGATAATCTCCTTCTAAAGGAGAGTTTGCTCGAAGATTTCAAGGGTTACTTG
 D  Q  L  D  N  L  L  L  K  E  S  L  L  E  D  F  K  G  Y  L 190        200        210        220        230        240
GGATGTCAGGCTCTTTCTGAGATGATCCAATTCTACCTAGAAGAGGTAATGCCACAGGCA
 G  C  Q  A  L  S  E  M  I  Q  F  Y  L  E  E  V  M  P  Q  A 250        260        270        280        290        300
GAAAACCAAGATCCTGATATTAAGGCACATGTTAATAGCCTCGGAGAGAACCTTAAGACT
 E  N  Q  D  P  D  I  K  A  H  V  N  S  L  G  E  N  L  K  T 310        320        330        340        350        360
CTAAGGTTGAGACTTCGTAGGTGCCACAGATTCCTACCCTGTGAAAATAAGAGTAAGGCT
 L  R  L  R  L  R  R  C  H  R  F  L  P  C  E  N  K  S  K  A 370        380        390        400        410        420
GTTGAACAAGTTAAGAACGCATTCAATAAGCTCCAGGAGAAGGGCATCTATAAGGCAATG
 V  E  Q  V  K  N  A  F  N  K  L  Q  E  K  G  I  Y  K  A  M 430        440        450        460        470        480
TCTGAGTTCGATATTTTCATTAATTACATAGAGGCTTATATGACAATGAAGATTCGTAAC
 S  E  F  D  I  F  I  N  Y  I  E  A  Y  M  T  M  K  I  R  N 490        500        510        520
CACCACCATCACCATCATAAGGATGAGTTGTAA
 H  H  H  H  H  H  K  D  E  L  *
```

METHOD OF TREATMENT OF GASTROINTESTINAL DISORDERS WITH IL-10

CROSS REFERENCE TO RELATED APPLICATION

This application claims the benefit of U.S. provisional patent application No. 61/418,481, filed Dec. 1, 2010, which is incorporated herein by reference in its entry.

FIELD OF THE INVENTION

The present invention concerns a method of treating inflammatory gastrointestinal disorders by oral administration, and a food product for the prevention or improvement of inflammatory gastrointestinal disorders and the like that uses IL-10 purified from transgenic rice expressing IL-10.

BACKGROUND OF THE INVENTION

Interleukin-10 (abbreviated to IL-10 in the following) is a cytokine produced mainly from several types of lymphocytes, such as type 2 helper T-cells (Th2), regulatory T-cells. Though the bioactivity thereof diverges greatly, the characteristic conspicuously varying from other cytokines is that its "inhibitory activity" has become the central issue. IL-10 has inhibitory control of immune function including the production of inflammatory cytokines such as IFN-γ (non-patent reference 1) and exhibits an inhibiting action indirectly towards lymphocytes via monocytic cells. That is, IL-10 exerts an anti-inflammatory effect in human body and maintains immune homeostasis. Its expression in mucous membranes such as the digestive tract is particularly distinguishing (non-patent reference 2). In human genome-wide analysis, the IL-10 signal shows an interrelation with intestinal disorders (non-patent references 3 and 4); the relationship inflammatory in gastrointestinal tract and the anti-inflammatory due to IL-10 is understood to be close and physiological (non-patent reference 5).

In this way, IL-10 is expected to inhibit inflammation and be a treatment drug for autoimmune disease (non-patent reference 6). If IL-10 can be manufactured in large quantities at a low cost using recombinant plant matter, we can expect the development of new use such as administering orally or spraying to mucosa of the nose.

In prior art, the synthesis of recombinant IL-10 is carried out by production using recombinant technology utilizing micro-organisms such as E. coli or mammalian cultured cells (the "method of prior art" as mentioned in the following); but, when mammalian cells are used as parasitic host cells, an enormous expense is involved in order to obtain a large quantity of recombinant IL-10, and the possibility of mixing pathogens such as viruses that infect humans, prion cannot be avoided. Further, the mixing toxicant such as endotoxins becomes a problem with recombinant IL-10 (non-patent reference 7). Particularly in the recombinant IL-10 purified by the method of prior art, the one which is endotoxin-free is not known up to now, and although the above-mentioned anti-inflammatory effect of IL-10 is known, this has not actually been applied in treatments of anti-inflammatory effect.

To solve these problems, the present inventors have considered a method for the expression of IL-10 in rice plants and the purification thereof. Examples in which humans are infected by plant viruses are not known, particularly rice plant is used in food for elderly by human, so as its safety has been confirmed. Accordingly, the risk of the mixing toxicant such as endotoxins is expected to be extremely low. Further, after recombinant rice plants expressing IL-10 are created once, the phylesis can be maintained by only cultivating these and recombinant IL-10 can be produced at extremely low cost in need of the cost for the cultivation only (patent reference 1 and non-patent references 8-9).

PRIOR ART REFERENCES

Patent References

[Patent Reference 1] JP 2010-183904

Non-Patent References

[Non-patent Reference 1] Annu. Rev. Immunol. 19: pp. 683-765 (2001)
[Non-patent Reference 2] Trends Immunol. 29: pp. 532-540 (2009)
[Non-patent Reference 3] Nat. Genet. 40: pp. 1319-1323 (2008)
[Non-patent Reference 4] N. Engl. J. Med. 361: pp. 2033-2045 (2009)
[Non-patent Reference 5] Gut 58: pp. 1173-1176 (2009)
[Non-patent Reference 6] Pharmacol Rev 55: pp. 241-69 (2003)
[Non-patent Reference 7] Naturwissenschaften 90: pp. 145-55 (2003)
[Non-patent Reference 8] Plant Biotechnology 5: pp. 84-92 (2007)
[Non-patent Reference 9] Protein Expression and Purification 72: pp. 125-130 (2010)

SUMMARY OF THE INVENTION

Problems to be Solved by the Invention

It is an object of the present invention is to provide a new method of treating inflammatory gastrointestinal disorders, which recombinant IL-10 is used.

Means for Solving the Problems

The present inventors have conducted intensive studies in an attempt to solve the above-mentioned problems looking at IL-10 expressed in rice plant seeds and took note that IL-10 expressed in rice plant seeds and purified is more suitable to be applied to the prevention and treatment by oral administration for the purpose of the prevention and treatment of inflammatory gastrointestinal disorders than prior IL-10. The inventors achieved to complete the present invention on the basis of this knowledge.

Accordingly, the present invention is as follows:
[1] A treatment method of inflammatory gastrointestinal disorders, wherein a recombinant IL-10 expressed in rice plant seeds is orally administrated.
[2] The method of above-mentioned [1], wherein the recombinant IL-10 is a purified recombinant IL-10.
[3] The method of above-mentioned [2], wherein the purification of recombinant IL-10 from rice plant seeds comprises the step of:
(1) extracting of recombinant IL-10 from seeds of recombinant rice plant using an extracting solution containing a reducing agent and a detergent;
(2) purifying of the extracted recombinant IL-10 by an affinity column.

[4] The method of above-mentioned [3], wherein the purification further comprises a step of (3) refolding of the purified recombinant IL-10.
[5] The method of above-mentioned [1], wherein the inflammatory gastrointestinal disorder is inflammatory bowel diseases.
[6] The method of above-mentioned [1], wherein the inflammatory gastrointestinal disorder is allergic enteritis.
[7] The method of above-mentioned [2], wherein the purified recombinant IL-10 is endotoxin-free.
[8] A pharmaceutical composition comprising a recombinant IL-10 expressed in rice plant seeds and a pharmaceutically acceptable carrier.
[9] The pharmaceutical composition of above-mentioned [8], which is for the prevention or treatment of inflammatory gastrointestinal disorders.
[10] A food product obtained by adding a recombinant IL-10 expressed in rice plant seeds.
[11] The food product of above-mentioned [10], which is for the prevention or improvement of inflammatory gastrointestinal disorders.
[12] A treatment method for inflammatory gastrointestinal disorders comprising orally administrating a food product obtained by adding a recombinant rice plant seed expressing recombinant IL-10 or the recombinant IL-10 expressed in the rice plant seeds.

Effects of the Invention

According to the method of the present invention, inflammatory gastrointestinal disorders can be effectively treated by a simple method. In particular, the IL-10 used in the present invention, expressed in rice plant seeds and purified, can be used very easily and effectively for many eligible patients as it can be administered orally to patients. Therefore the present invention, besides improving the treatment and prevention of inflammatory gastrointestinal disorders, is extremely beneficial over the improvement of prevention and treatment methods of prior art.

Also, the recombinant IL-10 expressed in rice seeds used in the present invention is endotoxin-free, and as it is characterized by being existed as a dimer, a higher anti-inflammatory effect can be expected when using it after purification.

The recombinant IL-10 expressed in rice seeds used in the method of the present invention can be used as an active ingredient in the fields of a prophylactic or therapeutic agent for inflammatory gastrointestinal disorders, a pharmaceutical composition for inflammatory gastrointestinal disorders, and a food product (supplements) for the prevention or treatment of inflammatory gastrointestinal disorders.

BRIEF DESCRIPTION OF THE DRAWINGS

FIG. 1 shows a base sequence (Seq ID no.: 1) and an amino acid sequence (Seq ID no.: 2) of the IL-10 gene that converted codon to a rice plant type.

DETAILED DESCRIPTION

Figure 2:
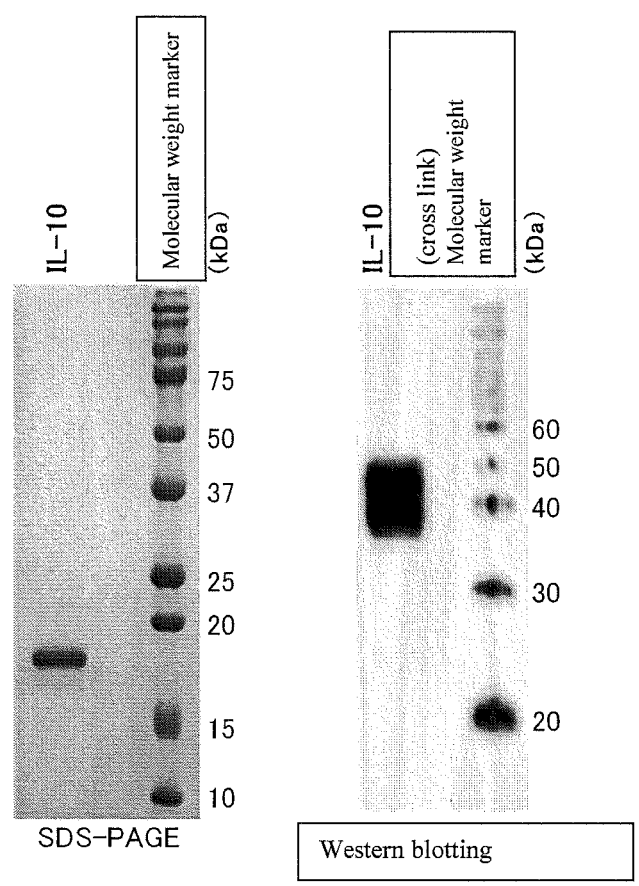
FIG. 2 shows that rice plant IL-10 which is the effective ingredient in the present invention is purified.

The present invention will be explained in more detail below.
1. Rice Plant IL-10
The "recombinant IL-10 expressed in rice plant seeds (cited in the following as "rice plant IL-10")" of the present invention means interleukin-10 (IL-10) expressed in recombinant rice plants which is manufactured using recombinant gene technology.

Though recombinant gene technology utilized in the manufacture of recombinant rice plants is not particularly limited as long as it is known method, for example, known transgenic methods can be applied (see Michio Matsuhashi et al., translation supervisor, *The Molecular Biology of Watson Recombinant DNA*, $2^{nd}$ ed., 1994, Maruzen; *Experimental Protocol of Model Plants*, 3rd revision (2005), Shimamoto, Okada, Tahata, general editors, Shujunsha, and the like).

More precisely, recombinant rice plants can be manufactured by introducing a gene coding for IL-10 into the appropriate expression vector, and introducing said vector into the rice plant cells.

The types of animals for using the rice plant IL-10 include, but not particularly limited to, vertebrates, preferably mammals, further preferably humans, mice, rats, guinea pigs, hamsters, rabbits, dogs, cats, sheep, pigs, cows horses and the like, particularly considering future applications, humans and mice are preferable, humans are more preferable (in the following IL-10 of human origin may be "human IL-10" and recombinant IL-10 expressed in rice plants for human IL-10 may be "human IL-10 from rice plant").

As the genetic sequence and amino acid sequence of the IL-10 used, the one which is recoded in Gene Banks (US NCBI) can be used. For example, in the case of human IL-10, it is recorded as BC104252 in the Gene Bank, and this genetic information and the like can be used.

The "recombinant IL-10" in the present invention, unless otherwise noted and as long as it has substantially the equivalent function to IL-10, is also included mutant thereof (including analog and homology.

The "mutant" means, for example, the one having a substitution, deletion or addition of 1 or several nucleotides in the nucleotide sequence of the IL-10 gene, or the one shows a percent identity with said nucleotide sequence, ordinarily more than 70%, preferably more than 80%, more than 85%, more preferably more than 90%, and further preferably more than 95%, more than 98%, more than 99%. The "percent identity" can be determined by accessing in the sequence database of a Gene Banks (US NCBI) and the like, and using a homology search algorithm of nucleic acids and proteins, such as BLAST and FASTA, and introducing a gap or not (for example, cf. Toshihisa Takagi and Minoru Kanehisa, eds., *Using the Genome Net Database*, $2^{nd}$ edition, 1998, Kyouritsu Publishing).

Said gene may be changed according to the codon frequency of the transformed rice plant.

In the present invention, a polypeptide derived from IL-10 or a polypeptide having substantially the equivalent function to IL-10 can be used instead of IL-10. As used herein, the "having substantially the equivalent function to IL-10" means that having substantially the function IL-10 has; for example, the function to have inhibitory control of the immune function, which includes the production of inflammatory cytokines, acting directly or indirectly on monocytes and lymphocytes; the function to stimulate induced differentiation of induced regulatory T-cells and the like.

The "polypeptide derived from IL-10" is not particularly limited as long as the polypeptide has the same amino acid sequence as part or all of the above-mentioned IL-10 complete long amino acid sequence (Seq ID no.: 2) and the polypeptide has the function IL-10 has; for example, the function to have inhibitory control of the immune function, which includes the production of inflammatory cytokines, acting directly or indirectly on monocytes and lymphocytes; the function to stimulate induced differentiation of induced regulatory T-cells and the like. These polypeptides are preferably shortened in order to adapt to drug discovery seeds. Such polypeptides are not limited as long as these have the above-mentioned function IL-10 has.

The "polypeptide having substantially the equivalent function to a polypeptide derived from IL-10" includes a polypeptide has the functions IL-10 has, which is same as the above-mentioned "polypeptide derived from IL-10"; for example, the function to have inhibitory control of the immune function, which includes the production of inflammatory cytokines, acting directly or indirectly on monocytes and lymphocytes; the function to stimulate induced differentiation of induced regulatory T-cells and the like, and in which 1 or several amino acids are deleted, added, substituted or rearranged in the amino acid sequence of the "polypeptide derived from IL-10". Here, though the number of amino acids deleted is not particularly limited, it is ordinarily 20 or less, preferably 10 or less, more preferably 5 or less, and most preferably 3 or less.

These polypeptides can be produced by peptide synthesis method generally known. The deletion, addition, substitution, or rearrangement of amino acids can be carried out by the methods generally known.

These polypeptides may be peptide-modified as long as they have the above-mentioned "substantially equivalent function to IL-10". Modifications of peptides include, for example, phosphorylation (e.g. Ser ($PO_3H_2$), Thr ($PO_3H_2$), Tyr ($PO_3H_2$), etc.), sulfation (e.g. Tyr ($SO_3H_2$), etc.), modification of the amino group (e.g. acetylation, succinylation, biotinylation, zincation, dinitrophenylation, dinitrosalicylation, myristoylation, etc.), modification of thiol group (e.g. farnesylation, granylation, etc.), modification by sugar (e.g. peptide containing Asn (GlcNAc), Ser/Thr (GalNAc), Ser/Thr (Gal-GalNAc), Ser/Thr (GlcNAc), Ser (Xyl), Thr (Man), etc.), modification of peptide combination (e.g. reduction type, statin type, etc.), fluorescent labeling (e.g. fluorescein isothiocyanation, dinitrosalicylation, Nma-ation, etc.), other labeling (e.g. biotin labeling, etc.), modification by fatty acids (e.g. DHA modification, etc.) and the like.

As expression vectors of IL-10 in rice plant seeds, vectors well known to a person skilled in the art can be used for introduction of IL-10 gene and expression of IL-10. For example, pUC-type vectors, pBR-type vectors, pBI-type vectors, pGA-type vectors and the like can be used. *Agrobacterium* binary vectors may also be used and these include, for example, pBinl9, pBI121, pGreen series, pCAMBRIA series, pPZP series, pPCV001, pGA482, pCLD04541, pBIBAC series, pYLTAC series, pSB11, pSB1, pGPTV series and the like. Besides these, virus vectors and the like can be used.

The vectors can be suitably contained signal sequences, tag sequences, protease identification sequences, selection markers and the like in addition to regulatory sequences such as promoters. Promoters are not particularly limited as long as they can drive the expression of the IL-10 gene in rice plant cells, for example, a cauliflower mosaic virus 35S promoter, rice plant actin gene promoter, glutelin promoter and the like can be used. Tag promoters are not limited as long as they can make the purification of expressed rice plant IL-10 easier, for example, 6-histidine, GST, MBP, HAT, HN, S, TF, Trx, Nus, biotin, FLAG, myc, RCFP, GFP and the like can be used. Protease recognition sequences are not particularly limited, for instance, recognition sequences such as Factor Xa, Thrombin, HRV, 3C protease can be used. Selected markers are not particularly limited as long as these can detect transformed rice plant cells, for example, neomycin-resistant genes, kanamycin-resistant genes, hygromycin-resistant genes and the like can be used.

For the transformation of rice plants using constructed expression vectors, known methods can be used. These include, for example, *agrobacterium* method, electroporation method, microinjection method, particle gun method and the like.

As for rice plants, any known plant of the rice plant family can be used. These include, for example, *Oryza sativa, Oryza ruffipogon, Oryza glaberrima, Oryza officinalis*, or *Oryza nivara* and the like, preferably, *Oryza sativa* subsp. *japonica* or *Oryza sativa* subsp. *indica*, more preferably, *Oryza sativa* subsp. *japonica*. Barley and corn of the rice plant family can also be used.

The "recombinant rice plant" in the present invention includes the all of the plant of the recombinant rice plant, a part of the recombinant rice plant (e.g. organs, tissue etc.), seeds of the recombinant rice plant, callus of the recombinant rice plant, cells of the recombinant rice plant, and/or shoots of the recombinant rice plant, preferably the seeds of the recombinant rice plant.

Though the rice plant IL-10 of the present invention is especially expressed in rice plant seeds, when extracting and purifying the rice plant IL-10 in rice plant seeds, it is impossible to extract using an aqueous buffer solution containing Tris or phosphoric acid and the like, which are used ordinarily in protein extraction, and a non-ionic detergent (in the following, this is designated that it is "hard extracted" and the like).

That is, though rice plant IL-10 is water soluble like known IL-10 as an individual property of recombinant IL-10, when expressed in recombinant rice plant, it is hard extracted because it adopt forms (not limited to these), such as; a storage form within a storage organ in the cells (protein granules, protein corpuscles) or an aggregate form; a form in which a proper disulfide combination within a peptide or between subunits is not formed; and a form not combined in another protein of the rice plant (for example, storage proteins containing several cysteines (such as prolamins, glutelins, etc.)).

Though the method for the extraction and purification of rice plant IL-10 of the present invention is not particularly limited, preferably, it can be carried out in conformity to the method mentioned in *Protein Expression and Purification* 72: pp. 125-130 (2010).

Figure 3:
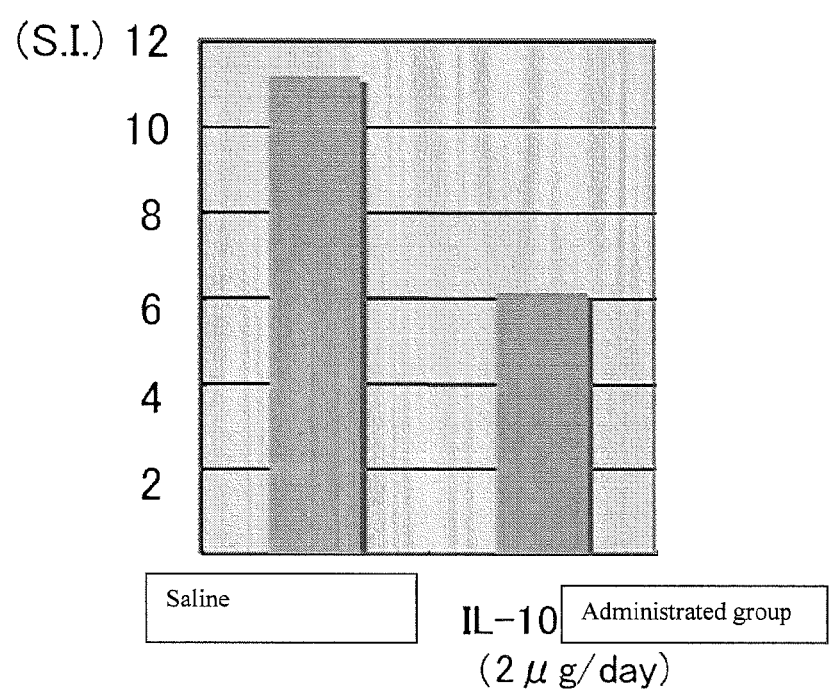
FIG. 3 shows the increase of small intestine Peyer's patch cells in inflammatory bowel disease model mice.
Figure 4:
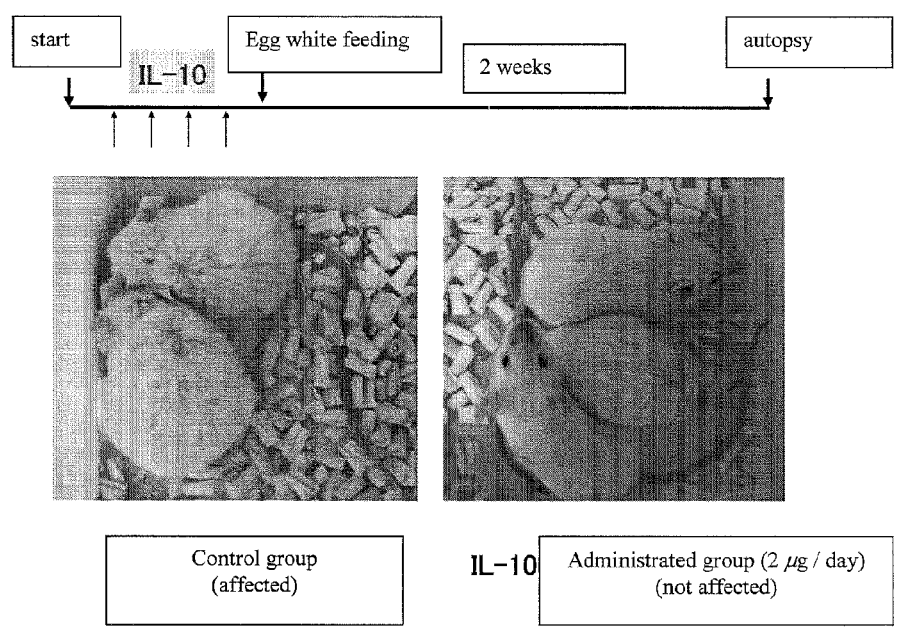
FIG. 4 shows inflammatory bowel disease model mice with a food allergy.

Specifically, the hard extracted rice plant IL-10 is extracted by combination use of a reducing agent and a detergent (see FIGS. 3 and 4). Using an extracting solution containing a reducing agent and a detergent, the hard extracted rice plant IL-10 can be extracted from recombinant rice plant that has been pulverized.

The extraction of rice plant IL-10 can be carried out, for example, under the following conditions.

The extracting solution used for the extract can be manufactured with the addition of a reducing agent and a detergent. A buffer solution consisting of the extracting solution includes a buffer solution selected from a Tris buffer solution, phosphoric acid buffer solution, Tricine buffer solution, HEPES buffer solution, MOPS buffer solution, carbonic acid buffer solution, citric acid buffer solution, boric acid buffer solution, MES buffer solution, and PIPES buffer solution. It can contain NaCl of 100-700 mM, preferably 500 mM, and have a pH of 6-10, preferably 7.4.

Though reducing agents are not particular limited as long as these are reducing agents capable of reducing disulfide combinations, these include, for example, dithiothreitol (DTT), reduction type glutathione (GSH), β-mercaptoethanol (bME), TCEP (tris(2-carboxethyl)phosphine hydrochloride), cysteine, mercaptoethylamine, mercaptopropionic acid and the like, preferably, DTT or bME, more preferably bME. The concentration of the reducing agent in the extracting solution can be fixed suitably at normally more than 1 mM, preferably more than 5 mM, more preferably more than 10 mM.

Though detergents are not particular limited as long as these are known detergents, these include, for example, non-ionic detergents such as Triton X-100, NP-40, Tween; zwitterionic detergents such as 7BzO, SB3-10, SB3-14, CHAPS, amidosulfobetaine-14 (ASB-14); and ionic detergents such as cetyltrimethylammonium bromide (CTAB), sodium dodecylsulfate (SDS). Among these, zwitterionic detergents and ionic detergents are preferable, ionic detergents are more preferable. Particularly, SDS and CTAB (most preferably, CTAB) can be used. The concentration of detergents in the extracting solution is normally 0.5-1.5 weight %, and preferably 1 weight %.

The rice plant IL-10 is extracted by adding the extracting solution, to which a reducing agent and a detergent have been added, to 1 g of pulverized recombinant rice plant at a ratio of about 10-50 ml, preferably about 15-30 ml and more preferably 20 ml.

For the extraction process, the method generally and previously known in the person skilled in the art can be adopted. Specifically, for example, the extracting solution to which a reducing agent and a detergent have been added is added to the pulverized recombinant rice plant, and the extraction is carried out mixing for several hours to 24 hours, preferably 8-12 hours, at low temperature (for example 4° C.). As needed, said extraction process may be done several times, for example: repeated twice.

When rice plant IL-10 is manufactured in the present invention, an extracting solution that does not contain a reducing agents and a detergent is used as needed before the above-mentioned extraction process, and proteins other than rice plant IL-10 hard extracted, that is, easily extracted impure proteins originating in the recombinant rice plant, can be extracted and removed from pulverized recombinant rice plant. Through this process, the purity of the rice plant IL-10 obtained can be enhanced to a great extent.

In said extraction process, the above-mentioned extracting solution, to which a reducing agent and a detergent have not been added, is added at a ratio of 10-50 ml, preferably 15-30 ml, more preferably 20 ml to 1 g of pulverized rice plant IL-10. The Extraction can be carried out in the same manner as above. After this, the supernatant is discarded by centrifugation and the extracting solution, to which the above-mentioned reducing agent and detergent are added, is added to the precipitate, and the rice plant IL-10 is extracted in the same manner as above.

Then, when using a combination of the two above-mentioned extraction methods, the extraction process using the extracting solution, in which the reducing agent and the detergent have not been added, is called the anterior-extraction, and the extraction process using the extracting solution, in which the reducing agent and the detergent have been added, is called the posterior-extraction.

Further, it is desirable to purify the rice plant IL-10 extracted by the above-mentioned extraction process as an active type IL-10.

In this purification process, rice plant IL-10 is purified in order to remove the detergent and impure proteins other than rice plant IL-10. Said purification can be carried out by a generally known method, it includes, for example, affinity, chromatography, ion exchange chromatography, size exclusion chromatography, hydrophobic interaction chromatography, immobilized metal affinity chromatography, hydroxyapatite chromatography and the like. These may also be used in suitable combinations. Among these it is preferable to purify using an affinity column suited to marker genes added to rice plant IL-10 in order to make the isolation and purification easier. Said purification process may be carried out several times as needed, for example, repeated twice.

Further, in the buffer solution used for the purification, a protein aggregate regulating agents such as guanidine hydrochloride may be added as needed.

Further in the purification process, a refolding process of the rice plant IL-10 may be combined. In the present invention, the "refolding" means that rewinding the rice plant IL-10 changed in the above-mentioned extraction process to an active native structure.

IL-10 has a pair of disulfide bonds in the monomer, and it functions to preserve the structure. This monomer forms a dimer combining by a non-covalent bond and becomes an active form. Thus, as these bonds irreversibly denature if they are destroyed, IL-10 cannot acquire activity.

Under the conditions of the above-mentioned extraction, rice plant IL-10 denatures by the by effect of the reducing agent and detergent. Thus, in order to obtain rice plant IL-10 having activity and native structure, the refolding process must be undertaken in addition to extraction process and purification process.

Refolding can be carried out by the methods known generally to a person skilled in the art. Normally, refolding is divided into the denaturation process and the refolding process. In order to increase the efficiency of refolding, it is preferable to carry out the respective processes under the following conditions.

Denaturation Process:

First, using a denaturation buffer solution, rice plant IL-10 is denatured. Though the composition of the denaturation buffer solution used here is not particularly limited, it includes buffer solutions such as Tris, HEPES, Tiricine and the like, and the buffer solution could contain 2-7 M, preferably 6 M of guanidine hydrochloride and 20-50 mM, preferably 30 mM of a reducing agent. The use of boric acid in the buffer solution is not preferred.

As reducing agent, known reducing agent that can reduce the disulfide bond (e.g. DTT, GSH, bME, etc.) can be used, preferably, DTT is used. The concentration of rice plant IL-10 that is solubilized in the denaturation buffer solution is suitable to a large extent, and added recombinant IL-10 is suitably pure to a high extent.

Denaturation temperature can be suitably chosen within the range of room temperature to 50° C. Denaturation time can be suitably chosen within a range of about 3-12 hours.

Refolding Process:

Though the composition of the buffer solution when refolding is not particularly limited, it includes the buffer solution such as Tris, HEPES, Tricine and the like, and the buffer solution could contain 0.2-2 mM, preferably 0.5 mM of an oxidizing agent and 0.1-2 M, preferably 0.6 M of a refolding agent. Use of boric acid in the buffer solution is not preferred. Said process may be carried out using the buffer solutions used in the above-mentioned denaturation process and adding the refolding agent to those.

As oxidizing agent, any oxidizing agent known to be able to reduce the thiol group (SH group) (for example, oxidization-type glutathione and cysteine and the like) can be used, preferably oxidation-type glutathione is used.

The "refolding agent" means a substance that stimulates refolding of proteins. Said refolding agents are not particularly limited as long as they have the function to stimulate refolding of proteins. These include arginyl, arginine amide, arginine ethyl ester, lysine, spermadine, spermine, guanidine, guanidinopropionic acid, glycine, proline, urea, sucrose, glucose, N-acetyl glucosamine, SDS, Tween 20, sodium sulfate, ammonium sulfate, ammonium iodide, ammonium thiocyanate, taurine, betaine, glyserol, polyol, β-alanine, trimethyl ammonium N-oxide, disaccharide, trehalose, polyethylene glycol, amino acid alkyl ester, amino acid amide, diamine, polyamine, imidazole, histadine and the like. Preferably the refolding agent is selected from the group consisting of arginine and its derivatives (for example, arginine ethyl ester, arginine amide, etc.). Salt (such as NaCl), enzymes (such as GloES, GLoEL, PDI, PPI) and the like may also be added to refolding buffer solution as needed. The quantity of refolding agent can be determined by the person skilled in the art.

The reaction temperature when using a refolding agent can be selected appropriately in the normal range of 4-50° C., preferably in the range of 33-42° C. The reaction time may be suitably chosen within the normal range of about 3-24 hrs, preferably 8-12 hrs.

Instead of a refolding buffer solution, refolding to a native structure is possible by "diluting" or "dialyzing" recombinant IL-10 added to the denaturation buffer solution in said denaturation process. The dilution magnification when diluting or dialyzing is more than 10-50 times volume, preferably more than 70 times volume, more preferably more than 90 times volume, and most preferably more than 100 times volume to the rice plant IL-10 solution (denaturation buffer solution). The pH of the dilution or the dialysis is preferably 8-9. The temperature of the dilution or dialysis is selected appropriately within the normal range of 4-50° C., preferably in the range of 33-42° C. The reaction time can be selected suitably within the range of about 3-24 hrs, preferably in the range of 8-12 hrs.

The rice plant IL-10 dimer obtained by refolding can be further purified using generally known methods (for example: affinity chromatography, ion exchange chromatography, size exclusion chromatography, hydrophobic interaction chromatography, immobilized metal affinity chromatography, and hydroxyapatite chromatography, and combinations of these). For example, the purification of the rice plant IL-10 dimer can be carried out using an anion exchange column. The rice plant IL-10 dimer may be attached to the anion exchange column resin if the pH of the buffer solution is 8.5-10.0, preferably a pH of 9.0. After this, by the flow of the pH 9.0 buffer solution containing salt (such as NaCl), the elution of the rice plant IL-10 from the column is possible. Tris buffer solution is preferable as the buffer solution to use in this purification. During the above-mentioned elution, the elution is obtained by the Gradient method using said buffer solution containing salt.

The rice plant IL-10 obtained thus can be verified by a known method. For example, the refolded rice plant IL-10 is cross linked using a cross linking reagent, and then, by carrying out SDS-PAGE and western blotting, it can be verified whether or not the rice plant IL-10 obtained is a dimeric active type IL-10 (Syto, et al., *Biochemistry* 37, 16943-51 (1998)).

Cross linking reagents include bis(sulfosuccinimidyl) suberate (BS3), Sulfo-EGS (ethylene glycolbis(sulfosuccinimidylsuccinate)), DTSSP (3,3'-dithiobis(sulfosuccinimidylpropionate)), DTBP (dimethyl 3,3'-dithiobispropionimidate dihydrocloride), DMS (dimethylsuberimidate dihydrocloride), DMP (dimethylpimelimidate dihydrocloride), DMA (dimethyladipimidate dihydrocloride) and the like. BS3 is preferable as a cross linking reagent of rice plant IL-10.

The rice plant IL-10 of the present invention has a very high percentage of active type IL-10 compared to generally known IL-10 and greater activity than generally known IL-10.

Through these processes, recombinant IL-10 can be purified from rice plant seeds.

The rice plant IL-10 obtained is differentiated from the recombinant IL-10 of prior art by its being endotoxin-free. As used herein, the "endotoxin-free" means that the purified rice plant IL-10 contains no endotoxins, or the content of endotoxins is below measurable limits; and, when rice plant IL-10 is administered orally, an endotoxin effect does not occur in the subject of the administration. Though measurement of endotoxins is not particularly limited as long as it is known method, for example, the measurement can be carried out using commercially available kits (Endospec ES-24 kit and EG reader SV-12; manufactured by SOikagaku Bio Business Co.).

As the rice plant IL-10 of the present invention is endotoxin-free, it is useful to be safely administered directly into the human body. Endotoxin-free human IL-10 from rice plant is particularly preferable for administration to humans.

2. Treatment of Inflammatory Gastrointestinal Disorders

The present invention provides a method for treatment of inflammatory gastrointestinal disorders, characterized by administrating the rice plant IL-10 orally.

As used herein, "inflammatory gastrointestinal disorders" is a general term for a chronic debilitating illness that long-term anorexia and diarrhea due to the occurrence of inflammation in the digestive tract such as the stomach and intestines is occurred to become wake. Symptoms thereof include weight loss, teeth grinding, mucous stool, green stool, tarry stool, granular stool, hepatitis, inflammation of the esophagus and the like. Gastrointestinal disorders include preferably inflammatory bowel diseases; specific names of said diseases include Crohn's disease and types of colitis such as ulcerative, granulomatous, ischemic, radioactive, and infectious colitis, intestinal tuberculosis, Behcet's disease and the like.

As used herein, the "inflammation", namely the "inflammation" which is object of the present invention, means the local reactions on the pathology consisting of kinetic complexes of cytological and histological reactions of the digestive tract tissues adjoining blood vessels, due to immunological reactions of the digestive tract that specifically leukocytes infiltrate from blood into external vascular tissue through rolling and adhesion on vascular endothelial cells in injuries or functional failure of the digestive tract due to various factors not limited to internal factors or external factors (bacterial infection; physical stimulation such as an external wound, heat, cold, radiation, electricity and the like; intake of allergenic substances; chemical substances, and the like), preferably means allergic inflammation.

Namely, the inflammatory gastrointestinal disorder that is the object of the present invention includes allergic enteritis (allergic gastroenteritis).

Rice plant IL-10 that is the active ingredient of the present invention, has exhibited a maximal effectiveness by oral administration in the treatment of inflammatory gastrointestinal disorders. As mentioned before, because rice plant IL-10 is an endotoxin-free IL-10, it can be administered safely to patients orally.

Though rice plant IL-10 administered orally in the method of the present invention is preferably rice plant IL-10 that has been purified in isolation by the above-mentioned extraction and purification methods, it may also be cultivated recombinant rice plant seeds. Further, said rice plant seeds may be administered orally after processing suitably for ingestion such as powdering to made into tablet.

The subjects of rice plant IL-10 administration in the method of the present invention include individuals (for example, mammals including humans, cows, horses, dogs, mice, rats, etc.) who have inflammation in the digestive tract, individuals who have a potential for inflammation in the digestive tract and the like.

In the method of the invention, the dosage of rice plant IL-10, the active ingredient for prevention and treatment of inflammatory gastrointestinal disorders, differs according to sex, symptoms, age, and administration method of the patient orally receiving it, but normally for an adult (body weight=60 kg) the dosage is 0.01 mg-5 mg per day, preferably 0.1 mg-1 mg per day. The daily dosage may be taken all at once or divided into several times per day regardless of before, after, or during meals. The period of administration is not particularly limited. Also, if rice plant IL-10 is ingested as rice plant seeds, the dosage of rice plant seed per day for an adult (body weight=60 kg) is normally 10 mg-500 g, preferably 100 mg-200 g.

In the method of the present invention, combination use of commonly known treatment drugs for inflammatory gastrointestinal disorders, such as antibiotics, steroids, antacids, internal medicines, immunosuppressives, etc., with rice plant IL-10 is possible. In this case, there is no limitation on timing of administration of rice plant IL-10 and contaminant drug, and these may be administered to subject simultaneously or at some interval. Rice plant IL-10 and the concomitant drug may be administered as 2 kinds of preparations containing respective active ingredients or a single preparation containing both active ingredients. The dose of the concomitant drug can be appropriately determined based on the dosage employed clinically. The combination ratio of the concomitant drug with rice plant IL-10 can also be selected suitably according to the subject, administration route, disorder in question, symptoms, kinds of combination and the like. For example, when the subject is a human, per 1 part by weight of the compound of the present invention, 0.01-100 parts by weight of the concomitant drug may be used.

For an antibiotic, metronidazole and the like can be exemplified. For a steroid, prednisolone and the like can be exemplified. For an antacid, ranitidine hydrochloride and the like can be exemprified. For an internal medicine, mesaladine, salazosulfapyridine, and the like can be exemplified. For an immunosuppressive, azathioprine and the like can be exemplified. Two or more kinds of concomitant drugs can be used at an appropriate combination ratio.

When rice plant IL-10 is used in combination with a concomitant drug, the reciprocal dosage can be decreased within a safe range in consideration of the adverse effects of these drugs. Especially, for immunosuppressives, steroids etc. the dosage can be lower than normal. Adverse effects that may be caused by these drugs can be safely prevented.

3. Anti-inflammatory Agent for Oral Administration

The present invention provides an agent with the effect of preventing or treating inflammatory gastrointestinal disorders (preferably, inflammatory enteritis) when administered orally, comprising the above-mentioned rice plant IL-10 as an active ingredient.

Rice plant IL-10, the active ingredient of the agent of the present invention, is as mentioned above. The content of rice plant IL-10 in the agent of the present invention differs according to form and dosage of rice plant IL-10, but it is, for example, about 0.1-100 weight %.

The drug form of the anti-inflammatory orally administrable agent of the present invention can adopt a general pharmaceutical form suitable for oral administration without limit; specifically granules, fine particles, tablets, powder, capsules, chewable tablets, liquids, suspensions, etc. can be exemplified. These can be formulated by the conventional methods, and as needed for the type of formulation, appropriate additives such as an excipient, disintegrant, lubricant, binding agent, coating agent, coloring agent, condensation inhibitor, absorption promoter, solubilizing agent, flavoring, sweetener, preservative, antioxidant, etc can be mixed.

Excipients include, but not particularly limited to, sucrose, lactose, glucose, corn starch, mannitol, crystalline cellulose, calcium phosphate, calcium sulfate and the like.

Disintegrants include, but not particularly limited to, starch, agar, calcium citrate, calcium carbonate, sodium hydrogen carbonate, dextrin, crystallizing cellulose, carboxymethyl cellulose, traganth and the like.

Lubricants include, but not particularly limited to, magnesium stearate, sodium stearate, stearic acid, calcium stearate, magnesium oleate, oleic acid, potassium oleate, capric acid, sodium stearyl fumarate, magnesium palminate, a combination of such lubricants and the like.

Binding agents include, but not particularly limited to, starch and its derivatives (pregelatinized starch, dextrin, etc.), cellulose and its derivatives (ethyl cellulose, carboxymethylcellulose sodium, hydroxypropylmethyl cellulose, etc.), gum Arabic, traganth, gelatin, sugars (glucose, sucrose, etc.), ethanol, polyvinyl alcohol and the like.

Coating agents includes, but not particular limited to, cellulose derivatives (hydroxypropylcellulose, cellulose acetate phthalate, hydroxypropylmethyl cellulose phthalate, etc.), shellac, polyvinylpyrrolidone, polyvinylpyridines (poly-2-vinylpyridine, poly-2-vinyl-5-ethylpyridine, etc.), polyvinyl acetal diethylaminoacetate, polyvinyl alcohol phthalate, metacrylate and metacrylic acid copolymers and the like.

Coloring agents are not particularly limited, and any coloring agent allowable for pharmaceuticals and food can be used. Blue no. 1, yellow no. 4, green no. 3, red no. 5, leek coloring, titanium dioxide, red cabbage coloring, red yeast coloring, purple potato coloring, gardenia coloring, cochineal coloring and the like can be exemplified.

Condensation inhibitors are not particularly limited, and any condensation inhibitors allowable for pharmaceuticals and food can be used. Stearic acid, talc, light anhydrous silicic acid, hydrous silicate dioxide and the like can be exemplified.

Absorption promoters include, but not particularly limited to, higher alcohols, higher fatty acids, detergents such as glycerin fatty acid ester and the like.

Solubilizing agents include, but not particularly limited to, adipinic acid, L-arginine, sodium benzoate, benzyl benzoate, esterified corn oil, ethanol, magnesium chloride, hydrochloric acid, olive oil, sodium carmellose, dry sodium carbonate, low-concentrate hydrochloric acid, citric acid, sodium citrate, glycine, glycerin, glycerin fatty acid ester, geraniol, sesame oil, cellulose acetate phthalate, sodium salicylate, magnesium oxide, α-cyclodextrin, β-cyclodextrin, γ-cyclodextrin, dibutylhydroxytoluene, tartaric acid, sucrose fatty acid esters, sodium hydroxide, sorbitan sesquioleate, sorbitan fatty acid esters, D-sorbitol, D-sorbitol solution, soy bean oil, soybean lecithin, sodium hydrocarbonate, sodium carbonate, medium-chain triglycerides, triacetin, sorbitan trioleate, nicotinic acid amide, lactic acid, concentrated glycerin, sucrose, hydroxypropylmethyl cellulose, castor oil, glacial acetic acid, glucose, propylene glycol, propylene glycol fatty acid esters, povidone, polyoxyethylene hydrogenated castor oil, polyoxyethylene (160) polyoxypropyline (30) glycol, polysorbate, polyvinyl alcohol, macrogol, D-mannitol, isopropyl myristate, anhydrous ethanol, anhydrous citiric acid, sorbitan monooleate, laurylmacrogol, lidocaine, phosphoric acid, sodium hydrophosphate, potassium dioxide phosphate and the like.

Stabilizers include, but not particularly limited to, benzoic acid, sodium benzoate, ethyl peroxybenzoate and the like.

Flavorings include, but not particularly limited to, and single flavoring agents, such as menthol, carvone, anethole, cineole, methyl salicylate, cinnamic aldehyde, eugenol, 3,1-menthoxypropane-1,2-diol thymol, linalool, linalyl acetate, limonene, menthone, menthyl acetate, N-substitute-para-menthane-3-carboxamide, pinene, octyl aldehyde, citral, pulegone, carbyl acetate, anise aldehyde, ethyl acetate, ethyl butylate, arylcyclohexane propionate, methyl anthranilate, ethylmethylethynyl glycidate, vanillin, undecalactone, hexanol, ethyl alcohol, propyl alcohol, butanol, isoamyl alcohol, hexenal, dimethylsulfide, cyclotene, furfural, trimethylpyrazone, ethyl lactate, ethylthioacetate, etc.; natural flavorings, such as peppermint oil, spearmint oil, anise oil, eucalyptus oil, wintergreen oil, *cassia* oil, clove oil, thyme oil, sage oil, lemon oil, orange oil, mint oil, cardamom oil, coriander oil, mandarin oil, lime oil, lavender oil, rosemary oil, laurel oil, chamomile oil, caraway oil, marjoram oil, bay leaf oil, lemon grass oil, *origanum* oil, pine needle oil, neroli oil, rose oil, jasmine oil, orris root concrete, absolute peppermint, absolute rose, orange flower, etc.; mixed flavors, such as strawberry flavor, apple flavor, banana flavor, pineapple flavor, grape flavor, mango flavor, butter flavor, milk flavor, tutti frutti flavor, tropical fruit flavor and the like.

Sweeteners include, but not particularly limited to, sodium saccharin, aspartame, stevioside, stevia extract, paramethoxycinnamic aldehyde, neohesperidin dihydrochalcone, parillartine and the like.

Preservatives include, but not particularly limited to, benzoic acid, sodium benzoate, ethanol, sodium edetate, dry sodium sulfite, citric acid, glycerin, salicylic acid, sodium salicylate, dibutyl hydroxytoluene, D-sorbitol, sorbic acid, potassium sorbate, sodium dihydroacetate, isobutyl paroxybenzoate, isopropyl paraoxybenzoate, ethyl paraoxybenzoate, butyl paraoxybenzoate, propyl paraoxybenzoate, methyl para-oxybenzoate, propylene glycol, phosphoric acid and the like.

Antioxidants include, but not particularly limited to, citric acid, citric acid derivatives, vitamin C and its derivatives, lycopene, vitamin A, carotenoids, vitamin B and its derivatives, flavonoids, polyphenols, glutathione, selenium, sodium thiosulfate, vitamin E and its derivatives, α-lipoic acid and its derivatives, pycnogenol, flavangenol, superoxide dismutase (SOD), glutathione peroxydase, glutathione-S-transferase, glutathione reductase, catalase, ascorbic acid peroxidase, mixtures of these and the like.

The orally administrable anti-inflammatory agent of the present invention is effective for inflammation in the digestive tract, preferably effective for inflammation in the small intestine (including duodenum, jejunum and ileum) or the large intestine (including cecum, colon, and rectum), and more preferably effective for inflammation in the large intestine.

The orally administrable anti-inflammatory agent of the present invention is useful for the prevention and/or treatment of inflammatory gastrointestinal disorders. In particular, it is useful for the prevention and/or treatment of inflammatory bowel diseases. The above-mentioned disorders are examples of inflammatory gastrointestinal disorders. For inflammatory bowel diseases, examples include Crohn's disease and large intestinal inflammation such as ulcerative colitis, granulomatous colitis, ischemic colitis, radiation enteritis, and infectious colitis.

The administration subjects for the orally administrable anti-inflammatory agent of the present invention include individuals (for example, mammals including humans, cows, horses, dogs, mice, rats, etc.) who have inflammation in the digestive tract, individuals who have a potential for inflammation in the digestive tract and the like.

The dosage of rice plant IL-10, which is the active ingredient of the orally administrable anti-inflammatory agent of the present invention, differs according to sex, symptoms, age, and administration method of the patient orally receiving said agent; but normally for an adult (body weight=60 kg), the dosage is 0.01 mg-5 mg per day, preferably an adult dosage of 0.1 mg-1 mg per day. The daily dosage may be taken all at once or divided into several times per day regardless of before, after, or during meals. The period of administration is not particularly limited.

It is possible to use above-mentioned known treatment drugs for inflammatory gastrointestinal disorders such as antibiotics, steroids, antacids, internal medicines, immunosuppressives and the like, in combination with the orally administrable anti-inflammatory agent of the present invention.

4. The Pharmaceutical Composition Comprising Rice Plant IL-10

The present invention provides a pharmaceutical composition that comprises rice plant IL-10 and a pharmaceutically acceptable carrier.

The rice plant IL-10, the active ingredient in the pharmaceutical composition of the present invention, is as described above. As used herein, the "pharmaceutically acceptable carrier", without being any commonly known carrier can be applied as the "pharmaceutically acceptable carrer" without being particularly limited; for example: carriers mentioned in *Remington's Pharmaceutical Sciences* and the like, or the "additives" given as examples for the above-mentioned medication of the present invention can be mentioned.

The content of rice plant IL-10 in the pharmaceutical composition of the present invention differs according to the drug form and dosage of rice plant IL-10, for example, the content is about 0.1-99 weight %.

Target disorders of the pharmaceutical composition of the present invention are not particularly limited but, in view of the characteristics of rice plant IL-10 as active ingredient, they are preferably inflammatory gastrointestinal disorders, particularly inflammatory bowel diseases (large intestinal inflammation such as Crohn's disease, ulcerative colitis, granulomatous colitis, ischemic colitis, radiation enteritis, and infectious colitis; intestinal tuberculosis, Behcet's disease etc.), and allergic enteritis (allergic gastroenteritis).

The administration method of pharmaceutical composition of the present invention is not particularly limited, but oral administration is desirable as the anti-inflammatory effect of the pharmaceutical composition of the present invention is maximized by oral administration.

When administering the pharmaceutical composition of the present invention, the dosage of the active ingredient, rice plant IL-10, differs according to sex, symptoms, age, and administration method of the patient receiving said pharmaceutical composition, but normally for an adult (body weight=60 kg), the dosage is 0.01 mg-5 mg per day, preferably an adult dosage of 0.1 mg-1 mg per day.

5. Food product for Preventing or Improvement of Inflammatory Gastrointestinal Disorders The present invention provides food products for the prevention or improvement of inflammatory gastrointestinal disorders, to which rice plant IL-10 is added. Prevention or improvement of inflammatory gastrointestinal disorders can be expected by ingesting the food product of the present invention or the rice seeds derived from the recombinant rice plant of the present invention.

Food products of the present invention may be any common forms of food to which the rice plant IL-10 of the present invention is added. For example, drinks such as soft drinks and powdered beverages can be provided by adding an appropriate flavoring. Specifically, the rice plant IL-10 of the present invention can be mixed in juice, milk, candy, jelly and the like and drunk or eaten. Such food products can be offered as food with health claims, and the food with health claims includes food or beverage products, particularly food with health claims, food for specialized health uses, and food with nutrient function claims and the like, marked as useful for the prevention or improvement of inflammation, which is what the invention is used for.

In addition, the food product of the present invention can be used as concentrated liquid food or food supplements. When used as a food supplement, it can be prepared in the form of tablets, capsules, powders, granules, suspensions, chewable tablets, syrups, etc. In the present invention, food supplements refer to a product which is ingested with the purpose of supplementing nutrition outside of other food intake nutritional supplements and other supplements are included in the food supplements.

When ingesting the food product of the present invention, the dosage of the active ingredient, rice plant IL-10, differs according to sex, symptoms, age, and administration method of the patient ingesting said food product, but normally for an adult (body weight=60 kg), the dosage is 0.01 mg-5 mg per day, preferably an adult dosage of 0.1 mg-1 mg per day.

Also, when ingesting rice plant IL-10 as rice plant seed for food, the dosage of rice plant seed per day for an adult (body weight=60 kg) is normally 10 mg-500 g, preferably 100 mg-200 g.

EXAMPLES

The present invention is explained in more detail in the following by referring to Examples and Comparative Examples, which are not to be constructed as limitative.

Example 1

Production of Recombinant Rice Plant Expressing Human IL-10

The production of recombinant rice plant was carried out according to the method mentioned in *Protein Expression and Purification* 72 (2010) pp. 125-130 and JP 2010-183904 A.

Specifically, in order to express the protein in rice plant seeds, a vector that expresses the recombinant gene by a glutelin promoter was used (see Yang, et al., *Plant Biotechnol J* 5, 815-26 (2007); JP 2008-109946 A). That is, based on the genetic sequence information of human IL-10 (Gene Bank accession No.: BC104252), a secretion signal is removed from human IL-10, the codons were converted according to the codon frequency in rice plant seed protein. The base sequence (Seq ID No.: 1) and the amino acid sequence (Seq ID No.: 2) of the human IL-10 gene in which the codons are converted to a rice plant type are shown in FIG. 1. The histidine-tag and the ER retention signal (KDEL) were added to the C terminal of said base sequence, the obtained product was ligated into an *agrobacterium* expression vector. pGPTV-35S-HPT-GluB1T was used as an *agrobacterium* expression vector. The vector includes a glutelin promoter (GluB-1P), secretion signal, and a glutelin terminator (GluB-1T). The human IL-10 gene was inserted downstream of the glutelin promoter and is designed to be expressed specifically in the endosperm of the rice plant seed.

Recombinant rice plant was produced by an ultra-rapid transformation method via *agrobacterium*. The above-mentioned expression vector was introduced into the *agrobacterium tumefaciens* EHA strain by electroporation. The rice plant (*Oryza sativa* cv Kitaake) mature seeds, 4-5 days after sowing, were treated for 3 days with transformed *A. tumefaciens*. Infected seeds were continuously cultured for 4 weeks in N6 selection medium containing hygromycin and MS regeneration medium, and then the seedlings regenerated from derived callus were transferred to a greenhouse.

Example 2

Extraction of Human IL-10

Extraction of human IL-10 was carried out according to the method mentioned in *Protein Expression and Purification* 72 (2010) pp. 125-130 and JP 2010-183904 A. Details are explained in the following.

(1) Anterior-Extraction

Rice seeds were collected from the above-mentioned recombinant rice plant. The hulls and chaff are removed from 50 g of seed and pulverized using an electric stone mill (SAMAP Co., F-50). The obtained product was applied to a 355 µM mesh sieve to remove the rice bran and germ parts, and recover the endosperm portions, and rice powder derived from endosperm portions were obtained. 40 g of the rice powder obtained was put into a 1 L flask, and 800 ml of an extracting solution (50 mM Tris (pH7.4), 0.5M NaCl) free of a reducing agent and detergent was added; extraction were conducted overnight at 400 rpm using a stirrer at 4° C.

(2) Posterior-Extraction

After centrifugally separating the extract of the anterior-extraction, the supernatent was removed and 800 ml of extracting solution (50 mM Tris pH 7.4, 0.5 M NaCl, 10 mM bME, 1% CTAB) containing a reducing agent and a detergent was added to the precipitate, and extraction was carried out for 6 hours at 4° C. using a stirrer as mentioned above.

The supernatant was collected after centrifugation (15000 g, 10 min), 800 ml of extracting solution containing both the above-mentioned reducing agent and the detergent was added to the precipitate and 2nd extraction were carried out the same as already mentioned. The supernatant was put into ice water for about 2 hours and CTAB was precipitated; this was removed using centrifugation (15,000 g, 10 min.) and a glass filter (Whatman, GF/A).

Figure 5:
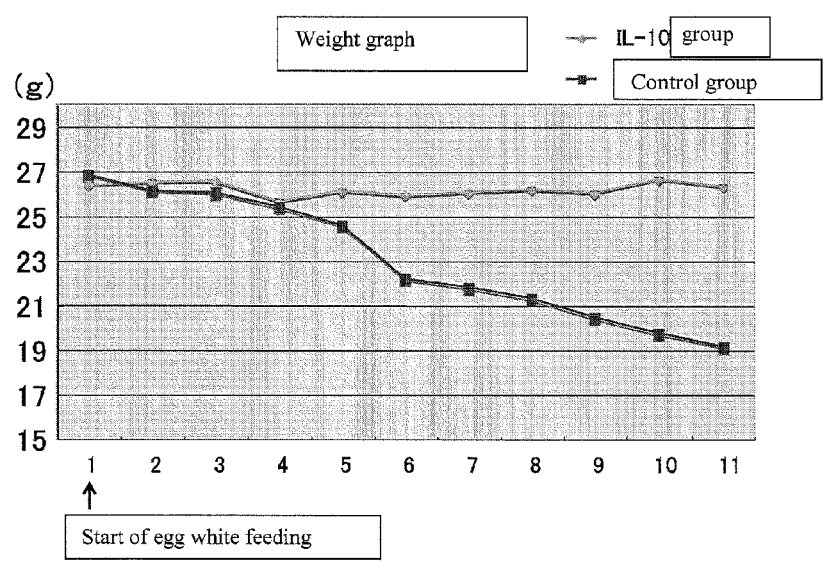
FIG. 5 shows the correlation the oral administration of rice plant IL-10 and body weight changes in inflammatory bowel disease model mice.

Human recombinant IL-10 was extracted by the process of said posterior-extraction (see FIG. 5).

Example 3

Purification of Human IL-10 from Rice Plant

Purification of the human IL-10 from rice plant was carried out according to the method mentioned in *Protein Expression and Purification* 72 (2010) pp. 125-130 and JP 2010-183904 A. Details are explained in the followings.

(1) Affinity Purification

Human IL-10 from rice plant was purified by affinity chromatography using histidine-tag affinity, utilizing AKTA prime plus (GE Healthcare).

The above-mentioned extraction product was applied to a HisTrapFF column (GE Healthcare). Then, using a starting buffer (50 mM Tris pH 7.4, 0.5 M NaCl, 20 mM imidazole) and an elution buffer (50 mM Tris (pH 7.4), 0.5 M NaCl, 0.4 M imidazole), human IL-10 was eluted by a stepwise elution method.

(2) Second Affinity Purification

Acetone was added to the elute obtained through the above-mentioned affinity column to produce a precipitate; the precipitate was dissolved in the same starting buffer as mentioned above containing 6 M guanidine hydrochloride and purified with the 1 ml HisTrapHP column (GE Healthcare). The same elution buffer containing 6 M guanidine hydrochloride was used as an elution buffer. The eluate was dialyzed against 10 mM Tris pH 7.4 to remove guanidine and acetone precipitation was performed.

(3) Refolding of Human IL-10 from Rice Plant

The precipitate obtained by adding acetone was dissolved for 3 hours at room temperature in a denaturing solution (6 M guanidine/50 m Tris pH 8.5/30 mM DTT). Then the solution obtained was diluted with a refolding buffer solution (50 mM Tris pH 8.5/0.5 mM oxidized glutathione/0.6 M arginine hydrochloride) at a dilution rate of 20-40 times and left overnight at a temperature of 33-42° C.

An evaluation of refolding was carried out by detecting IL-10 dimer. Samples containing human IL-10 from rice plant were chemically cross-linked and dimmer of human recombinant IL-10 was detected by SDS-PAGE and western blotting (cf. Syto et al., *Biochemistry* 37, 16943-51 (1998)). The cross-linking reaction was carried out for 30 minutes at room temperature by adding 10 µl of 0.4 M sodium bicarbonate buffer solution (pH 8.5) containing 2 mM BS3 to 10 µl of a refolded sample (protein concentration: 0.1 mg/ml or less); then, the reaction was stopped by adding in 1 µl of 1M Tris pH 8.0.

Refolding could be carried out at a high efficiency of 10% or more by said process.

The refolded human IL-10 from rice plant was dialyzed against a buffer solution consisting of PBS and 50 mM Tris (pH 9.0) for 2 days.

When a precipitate was generated, it was removed by centrifugation and the supernatant was subjected to the following anion exchange column purification.

(4) Purification by Ion Exchange Column

Samples obtained after refolding were refined using the anion exchange column HiTrapQ (5 ml; GE Healthcare). The sample was subjected to the above-mentioned column and human IL-10 from rice plant was eluted by the Gradient elution method, using a starting buffer (50 mM Tris (pH 9.0)) and an elution buffer (50 mM Tris (pH 9.0)/0.5 M NaCl).

The sample given by the elution fraction obtained by the above-mentioned ion exchange column purification was subjected to the above-mentioned cross linking reaction to detected human IL-10 from rice plant. Consequently, the separation of dimeric human IL-10 from rice plant was confirmed. The results are shown in FIG. 2.

Then, the elution fraction obtained by the above-mentioned ion exchange column purification was concentrated and subjected to the cation exchange column in order to remove a slight remaining impurity. The elution fraction containing dimeric human IL-10 from rice plant was dialyzed against 50 mM MES (pH 6.5) and purified using a cation exchange column HiTrap SP 1 ml (GE Healthcare). The dialyzed solution was subjected to the above-mentioned column, and human IL-10 from rice plant was eluted by the gradient elution method using a starting buffer (50 mM MES (pH 6.5)) and elution buffer (50 mM MES (pH 6.5)/0.5 M NaCl).

(5) Gel Filtration Column Purification

Gel filtration column purification was carried out to separate dimeric human IL-10 from rice plant from slightly remaining monomer. A HiPrep 16/60 Sephacryl S-100 HR (GE Healthcare) was used with a 50 mM sodium phosphate (pH 7.4)/150 mM NaCl buffer. Two peaks were observed, and as a result of analysis by the cross lining reaction, the separation of the dimeric human IL-10 from rice plant and monomer was confirmed. The results are shown in FIG. 2.

(6) Measurement of Biological Activity

The biological activity of the purified dimeric human IL-10 from rice plant was examined using MC 9 cells derived from mouse mast cells.

Since MC/9 cells are activated in the coexistence of IL-4 and IL-10, the quantification of IL-10 is possible by culturing MC/9 cells in the presence of IL-4 and a sample, and comparing the obtained activation state of MC/9 cells with those of standard IL-10. MC/9 cells were cultivated with DME, 10% FCS. Then, the cell suspension was dispensed into 96 well plates, 50 µl per well ($1-2 \times 10^4$ cells/per well), and a 50 µl sample containing 20 ng/ml of IL-4 was added; cells were cultured for 72 hours at 37° C. Then, 10 µl of Alamar Blue was added, cells were further cultured for 4 hours, and absorbance of 570 nm was measured with a microplate reader (BIO-RAD, Model 1680). As a result of the bioactivity measurement using MC 9 cells, the ED 50 of the purified dimeric human IL-10 from rice plant was 2 ng/ml or less, and it was shown to have equal bioactivity to the molecules in the human body.

Further the endotoxin level was measured with an endotoxin detection kit (Endospec ES-24S kit and EG reader SV-12; Seikagaku BioBusiness Co.), the endotoxin level was 0.0001 EU/µg or less and for below the endotoxin level of human IL-10 produced by *E. coli* which was conceived to be around 1 EU/µg.

From the above results, the 2.1 mg of active dimeric human IL-10 was purified from 40 g of rice plant seed at 4.3% recovery rate to a total rice-extracted protein by the method of the present invention.

Example 4

Induction of Immune Tolerance in Inflammatory Bowel Disease Model Mice

For ovalbumine-specific T cell receptor transgenic mice (DO 11.10 mice), oral immune tolerance can be induced by a continuous feeding of egg whites. It is known that hypoproliferative regulatory T cells are induced in immune organs such as small intestinal Peyer's patches due to this immune tolerance.

After feeding an egg white diet to the DO 11.10 mice, the small intestinal Peyer's patch cells were collected and the proliferation response of antigen (ovalbumin) specific small intestinal Peyer's patch cells (PP) was measured. Human IL-10 from rice plant dissolved in saline was administered into the stomach (2 µg/day) with oral sonde. On the one hand, saline was administered orally to the control group. The results are shown in FIG. 3.

The proliferation of small intestinal Peyer's patch cells of the human IL-10 from rice plant administration group was lower compared to the control group. From this result, it was elucidated that, the mucosal immune organs were certainly affected by administered human IL-10 from rice plant and immune response potential of the organ was changed.

Example 5

Evaluation of Digestive Tract Inflammation in Inflammatory Bowel Disease Model Mice Ovalbumine-specific T cell receptor transgenic mice (OVA 23.3 mice), develop food allergic enteritis by continuous feeding of ovalbumin. In vivo Anti-inflammatory effect of the human IL-10 from rice plant was evaluated by using the food allergy model mice.

Human IL-10 from rice plant dissolved in saline was administered into the stomach of 23.3 mice for 4 days (2 μg/day) using an oral sonde. Only the saline solution was administered to the control group. Then feed was exchanged to an egg white diet (20% egg white) mice were maintained under free-feeding condition and measurement of body weight, and observation of condition were carried out for 2 weeks consecutively. The results are shown in FIGS. 4 and 5.

The control group, after changing to the egg white diet, developed a food allergy and a decrease in body weight was observed. On the other hand, in the group that was orally administered human IL-10 from rice plant, after changing to the egg white diet, their physical condition was maintained and decrease in the weight was not observed.

Figure 6:
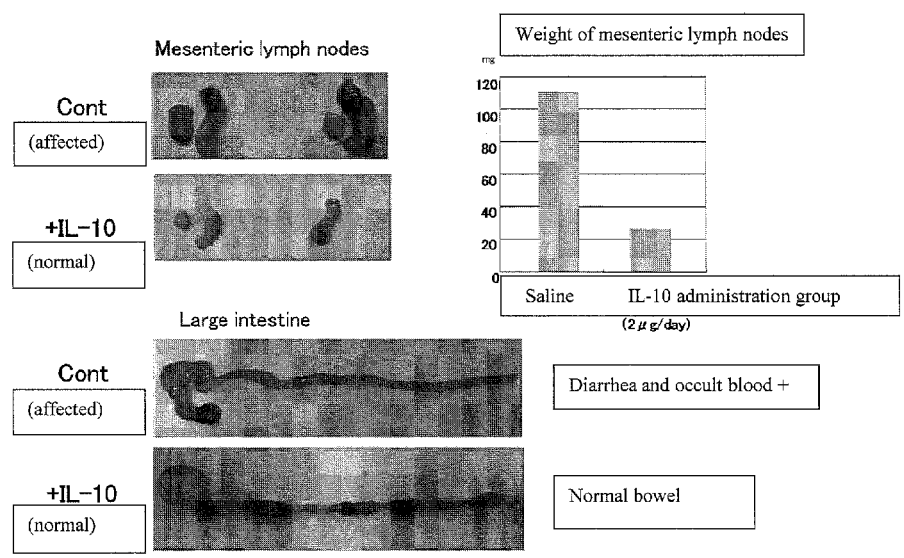
FIG. 6 shows the influence of oral administration of rice plant IL-10 to inflammatory bowel disease model mice on the digestive system.

Further, mice of the control group and the human IL-10 from rice plant oral administration group were euthanized, the digestive tract was autopsied. The results are shown in FIG. 6.

In the large intestines of the 23.3 mice with food allergy developed, runny bowels and hemorrhages were observed. Swelling and weight increase of the mesenteric lymph nodes were also observed. On the other hand, the digestive tract of the human IL-10 from rice plant oral administration group was respectively normal.

Example 6

Measurement of Cytokine in Inflammatory Bowel Disease Model Mice

Figure 7:
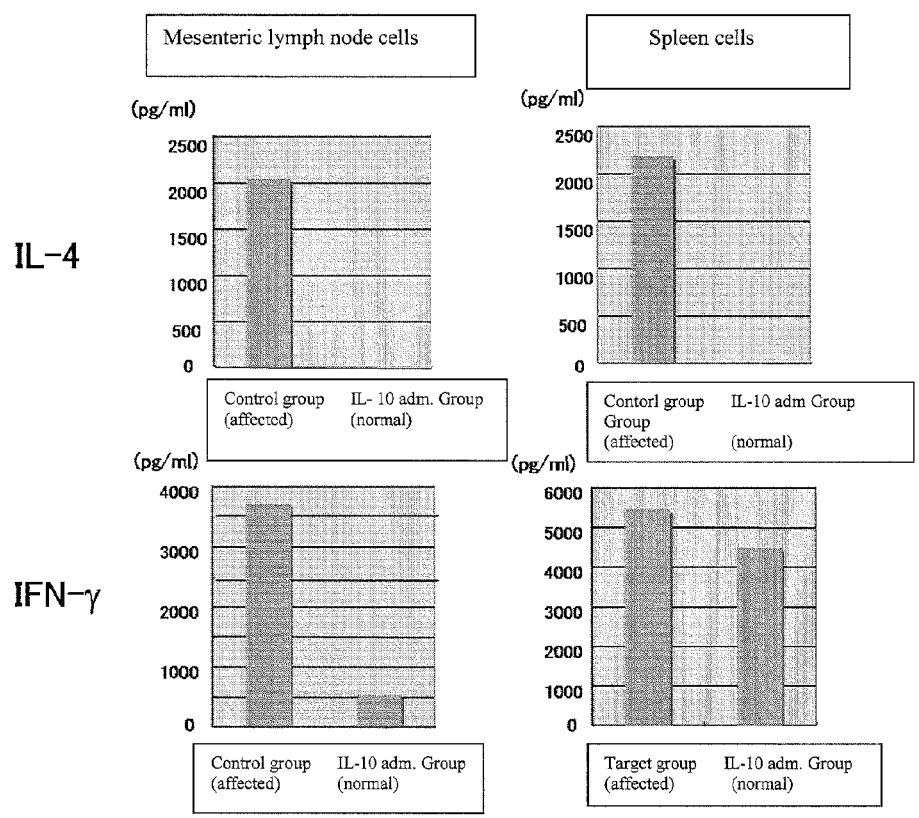
FIG. 7 shows the cytokine production in mesenteric lymph nodes and spleen cells of inflammatory bowel disease model mice.

Human IL-10 from rice plant dissolved in a saline or saline, was administered orally to 23.3 mice by the same method as in Example 3, and then egg white diet was fed. Following that, the mesenteric lymph nodes and spleen cells of each mouse were collected, and the respective cells were cultured for 3 days in the presence of antigen (ovalbumin). The culture supernatant of the cells was collected and cytokine ELISA was carried out for IL-4 and IFN-γ using a commercially available kit (Mouse Cytokine ELISA kit; R & D Systems). The results are shown in FIG. 7.

Allergic enteritis in 23.3 mouse is known to occur mainly by a Th2 reaction (overproduction of IL-4 due to type 2 helper T cells). In the cells from the control group with allergic symptoms, the production of IL-4 was significantly high in the mesenteric lymph node and spleen cells. On the other hand, in the human IL-10 from rice plant oral administration group, the production of IL-4 was suppressed at low level. For the production of IFN-γ, however, a difference was observed only in the mesenteric lymph nodes.

From the results above, the followings can be understood;
1) acute toxicity due to oral administration of human IL-10 from rice plant was not observed;
2) eating disorder due to oral administration of human IL-10 form rice plant was not observed;
3) allergy symptoms in the digestive tract are improved due to oral administration of human IL-10 from rice plant;

Namely, the safety and usefulness for inflammatory gastrointestinal disorders of human IL-10 from rice plant produced by recombinant rice plants were elucidated.

While the invention has been described with an emphasis on preferred embodiments, but it will be obvious to a person skilled in the art to modify the preferred embodiments within the range where the effects of the present invention can be exhibited. The present invention has the intention that the invention may be practiced otherwise than as specifically described herein. Subsequently, the present invention includes all modification encompassed within the spirit and scope of the invention as defined by the following "claims".

The contents disclosed in any publication cited herein, including patents and patent publications, are hereby incorporated in their entireties by reference, to the extent that they have been disclosed herein.

INDUSTRIAL FIELD OF APPLICATION

According to the present invention, inflammatory gastrointestinal disorders can be effectively treated by a simple method. In particular, the recombinant IL-10 used in the present invention, expressed in rice plant seeds and purified, can be used very easily and effectively for many eligible patients as it can be administered orally to patients. Therefore the present invention, besides improving the treatment and prevention of inflammatory gastrointestinal disorders, is extremely beneficial over the improvement of prevention and treatment methods of prior art.

Also, the recombinant IL-10 expressed in rice seeds used in the present invention is endotoxin-free, and as it is characterized by being existed as a dimer, a higher anti-inflammatory effect can be expected when using it after purification.

The recombinant IL-10 expressed in rice plant seeds used in the method of the present invention can be used as an active ingredient in the fields of a prophylactic or therapeutic agent for inflammatory gastrointestinal disorders, a pharmaceutical composition for inflammatory gastrointestinal disorders, and a food product for the prevention or treatment of inflammatory gastrointestinal disorders.

What is claimed is:

1. A treatment method for an inflammatory gastrointestinal disorder, wherein a recombinant IL-10 expressed in rice plant seeds is orally administrated following isolation and purification.

2. The method of claim 1, wherein the purification of recombinant IL-10 from rice plant seeds comprises the steps of:
   (1) extracting the recombinant IL-10 from seeds of recombinant rice plants using an extracting solution containing a reducing agent and a detergent; and
   (2) purifying the extracted recombinant IL-10 by an affinity column.

3. The method of claim 2, wherein the purification further comprises a step of (3) refolding the purified recombinant IL-10.

4. The method of claim 1, wherein the inflammatory gastrointestinal disorder is inflammatory bowel disease.

5. The method of claim 1, wherein the inflammatory gastrointestinal disorder is allergic enteritis.

6. The method of claim 1, wherein the purified recombinant IL-10 is endotoxin-free.

7. The method of claim 1, wherein said recombinant IL-10 expressed in rice plant seeds is orally administrated in a form selected from the group consisting of granules, fine particles, tablets, powders, capsules, chewable tablets, liquids and suspensions.

8. A treatment method for inflammatory gastrointestinal disorders comprising orally administrating an effective amount of a food product comprising or containing a recombinant rice plant seed expressing recombinant IL-10 or the recombinant IL-10 expressed in the rice plant seeds.

* * * * *

SEQUENCE LISTING

<160> NUMBER OF SEQ ID NOS: 2

<210> SEQ ID NO 1
<211> LENGTH: 513
<212> TYPE: DNA
<213> ORGANISM: Homo sapiens

```
<220> FEATURE:
<221> NAME/KEY: CDS
<222> LOCATION: (1)..(513)
<223> OTHER INFORMATION: Codon was converted to a rice plant type

<400> SEQUENCE: 1 agt cca ggc caa gga act cag tct gaa aat agc tgc aca cac ttc cct      48
Ser Pro Gly Gln Gly Thr Gln Ser Glu Asn Ser Cys Thr His Phe Pro
1               5                   10                  15 ggc aat ctc cca aac atg ctt cgt gat ttg agg gat gca ttc agt cgt      96
Gly Asn Leu Pro Asn Met Leu Arg Asp Leu Arg Asp Ala Phe Ser Arg
            20                  25                  30 gtt aag acc ttc ttt caa atg aag gat caa cta gat aat ctc ctt cta     144
Val Lys Thr Phe Phe Gln Met Lys Asp Gln Leu Asp Asn Leu Leu Leu
        35                  40                  45 aag gag agt ttg ctc gaa gat ttc aag ggt tac ttg gga tgt cag gct     192
Lys Glu Ser Leu Leu Glu Asp Phe Lys Gly Tyr Leu Gly Cys Gln Ala
50                  55                  60 ctt tct gag atg atc caa ttc tac cta gaa gag gta atg cca cag gca     240
Leu Ser Glu Met Ile Gln Phe Tyr Leu Glu Glu Val Met Pro Gln Ala
65                  70                  75                  80 gaa aac caa gat cct gat att aag gca cat gtt aat agc ctc gga gag     288
Glu Asn Gln Asp Pro Asp Ile Lys Ala His Val Asn Ser Leu Gly Glu
                85                  90                  95 aac ctt aag act cta agg ttg aga ctt cgt agg tgc cac aga ttc cta     336
Asn Leu Lys Thr Leu Arg Leu Arg Leu Arg Arg Cys His Arg Phe Leu
            100                 105                 110 ccc tgt gaa aat aag agt aag gct gtt gaa caa gtt aag aac gca ttc     384
Pro Cys Glu Asn Lys Ser Lys Ala Val Glu Gln Val Lys Asn Ala Phe
        115                 120                 125 aat aag ctc cag gag aag ggc atc tat aag gca atg tct gag ttc gat     432
Asn Lys Leu Gln Glu Lys Gly Ile Tyr Lys Ala Met Ser Glu Phe Asp
130                 135                 140 att ttc att aat tac ata gag gct tat atg aca atg aag att cgt aac     480
Ile Phe Ile Asn Tyr Ile Glu Ala Tyr Met Thr Met Lys Ile Arg Asn
145                 150                 155                 160 cac cac cat cac cat cat aag gat gag ttg taa                         513
His His His His His His Lys Asp Glu Leu
                165                 170

<210> SEQ ID NO 2
<211> LENGTH: 170
<212> TYPE: PRT
<213> ORGANISM: Homo sapiens

<400> SEQUENCE: 2

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110
```

```
Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

His His His His His His Lys Asp Glu Leu
                    165             170
```